United States Patent

Carchidi et al.

[11] Patent Number: 6,138,539
[45] Date of Patent: Oct. 31, 2000

[54] TORQUE RATCHET TOOL PARTICULARLY USEFUL WITH ENDOSSEOUS DENTAL IMPLANTS

[75] Inventors: Joseph Edward Carchidi, West Bridgewater, Mass.; Alan R. Balfour, Petaluma, Calif.

[73] Assignee: ACE Surgical Supply Co., Inc., Brockton, Mass.

[21] Appl. No.: 09/378,609

[22] Filed: Aug. 21, 1999

Related U.S. Application Data

[60] Provisional application No. 60/098,131, Aug. 27, 1998.

[51] Int. Cl.[7] .................................................. B25B 23/159
[52] U.S. Cl. .................................. 81/467; 81/471; 81/472
[58] Field of Search .............................. 81/467, 471, 472, 81/477–478, 483

[56] References Cited

U.S. PATENT DOCUMENTS 2,766,648  10/1956  Jazwieck ..................................... 81/58
5,129,293   7/1992  Larson et al. .......................... 81/478 X

*Primary Examiner*—David A. Scherbel
*Assistant Examiner*—Anthony Ojini
*Attorney, Agent, or Firm*—John A. Haug

[57] ABSTRACT

A dental torque ratchet head and driver handle (8) is formed with a chamber (12a) between first (30) and second (32) pivotably mounted handle members which receives a plastic insert (14) formed in a configuration selected so that the insert fractures at a selected torque to thereby ensure the application of a precalibrated level or torque to an abutment or prosthetic screw of an implant. A solid metal insert (14') can be used to convert the tool to a straight ratchet tool.

11 Claims, 3 Drawing Sheets

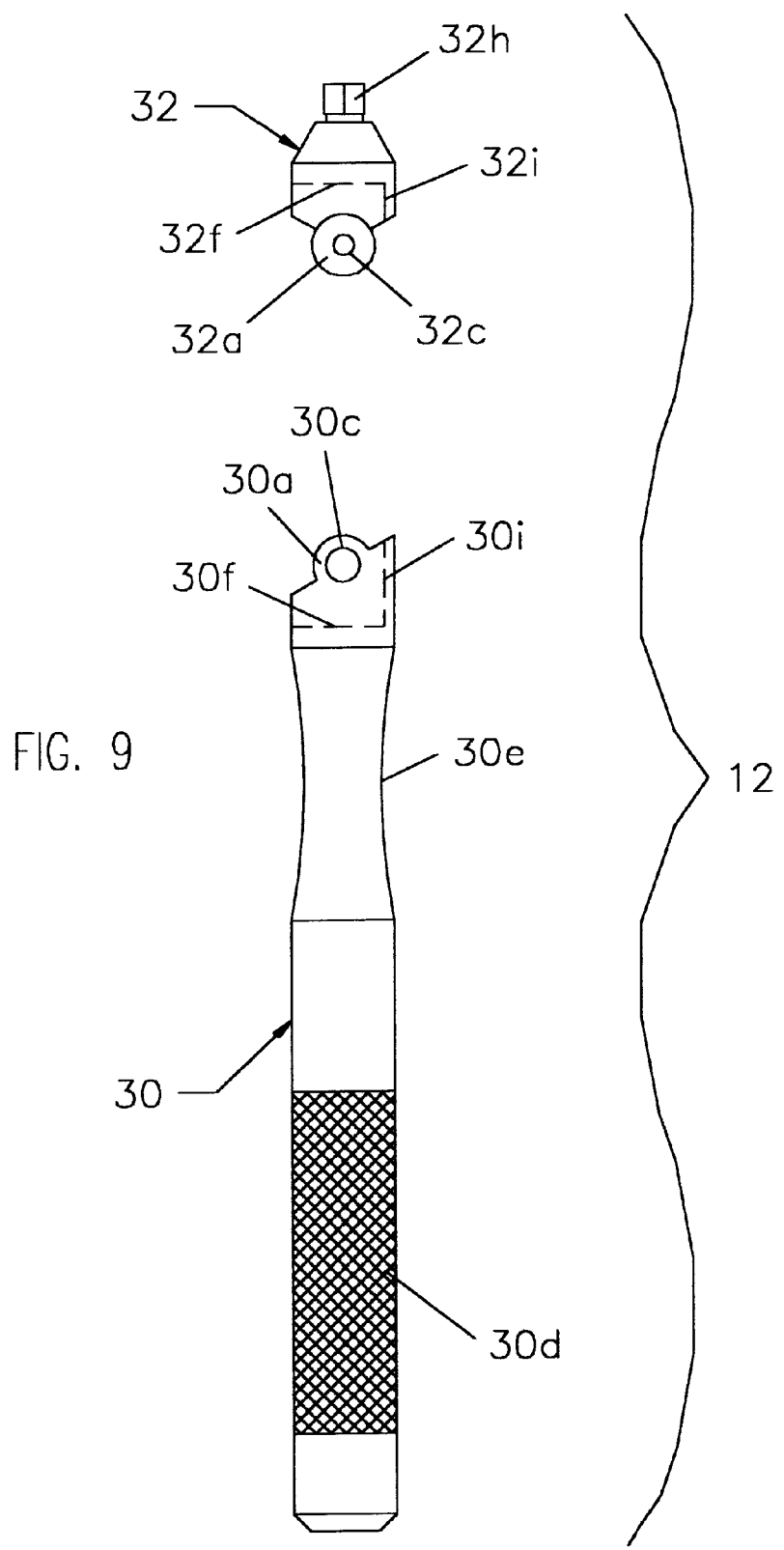

TORQUE RATCHET TOOL PARTICULARLY USEFUL WITH ENDOSSEOUS DENTAL IMPLANTS

RELATED APPLICATIONS

Benefit is claimed of U.S. Provisional Application Ser. No. 60/098,131, filed Aug. 27, 1998.

This invention relates generally to surgical and prosthetic tools used to deliver and assemble screws and abutments into dental implants and related components and particularly to precalibrated dental torque ratchet wrenches.

BACKGROUND OF THE INVENTION

The invention addresses problems associated with the delivery and assembly of abutments screws into dental implants and related components using a conventional torque ratchet wrench. Most dental implants currently used are manufactured with a bore having an internal machine screw thread to accept and retain an abutment or prosthetic screw. However, due to the intrinsic nature of a thread design, if components are not assembled with the system's required tunctional torsional preload, the abutment or screw will loosen from the implant. Once loose, the abutment or screw is at risk of failure as all the functional loads end up being applied directly to the thread itself.

To prevent such thread attachment from coming loose, the prosthetic restoration is assembled into the implant with a torsional preload to resist the opening of the assembled joint during normal functional loading, i.e. chewing. This assembly is accomplished by using a torsional screw driver or wrench. As a means to regulate the applied preload of the assembled joint, the industry has developed several, spring actuated, mechanical break-a-way neck hand held torque wrenches. In addition to providing the assembled implant/prosthetic joint with the correct pre-load for eliminating joint separation, these break-a-way torque wrenches are used to prevent stripping or fracturing of the screw thread or overloading the implant during assembly.

Although these tools meet the stated functional requirements, continuous wear of the internal moving parts of the break-a-way head, due to their mechanical design, causes such tools to drift out of calibration over time and use. In fact, information accompanying most of the vailable tools state that the tools must be recalibrated at least once a year as part of the maintenance program for the tools. Since these tools use a mechanical spring to apply the desired application of torque, sterilizing the tools with steam autoclaving has lead to corrosive binding ot the break-a-way neck. Once locked, these wrenches are unable to control the application torque applying the preload. Furthermore, based on the predetermined application preload needed to prevent opening of the assembled implant/prosthesis joint, an uncontrolled variation in the application torque may lead to fracture or failure of the prosthesis. These conditions give rise to concerns for these tool's long term replacement costs, dependable function over time, sterility requirements and overall reliability.

SUMMARY OF THE INVENTION

An object of the present invention is to provide a tool which overcomes the above noted deticiencies in the prior art at a reasonable cost to the industry. Another object of the invention is to provide a torsion application tool that consistently applies the desired predefined application torque. It is a further object of the invention to provide a tool that is not subject to constant recalibration requirements or sterility issues and one which can be used predictably over time. it is a further object of the invention to provide a tool which meets the size requirements for use in oral cavities.

Briefly, in accordance with the present invention, a torque ratchet tool, having a pivot arm driver handle, houses a precalibrated disposable insert which transfers an applied force to consistently deliver a predetermined torque application and correctly preload the prosthetic attachment to the implant. Each disposable insert is manufactured from a plastic material that has been machined to a specific dimensional size and fractures at a predefined application torque. The invention solves the problems of calibration requirements and allows the users to effectively apply the predetermined seating torque in a sterile, cost effective, simple, easy to use and functionally reliable manner. Additionally, if the pre-defined application torque is not necessary, a solid metal insert can be used and the tool will function as a straight ratchet tool. These and other objects and features will become apparent from the following description taken together with the accompanying drawings in which like reference numerals refer to like parts throughout the several views.

BRIEF DESCRIPTION OF THE DRAWINGS

FIG. 9 is a top plan view of separate portions of the pivot arm driver handle shown in FIGS. 1–3.

DETAILED DESCRIPTION OF THE PREFERRED EMBODIMENT

Figure 1:
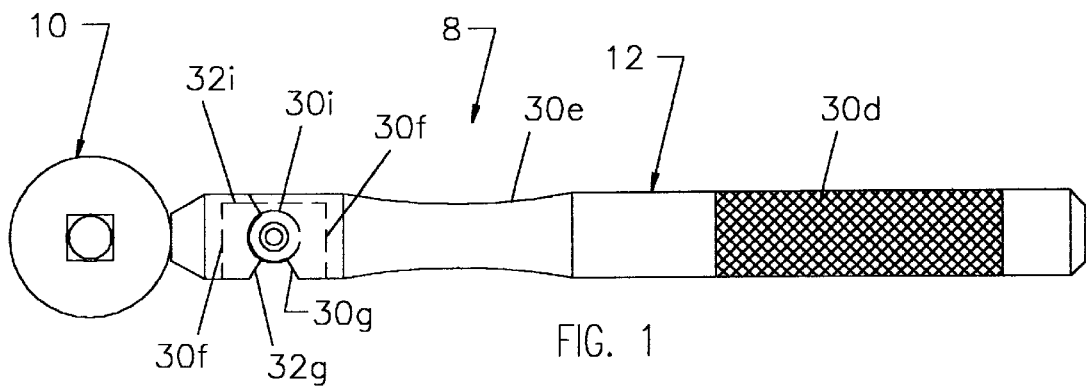
FIG. 1 is a top plan view of a torque ratchet tool made in accordance with the invention.
Figure 2:
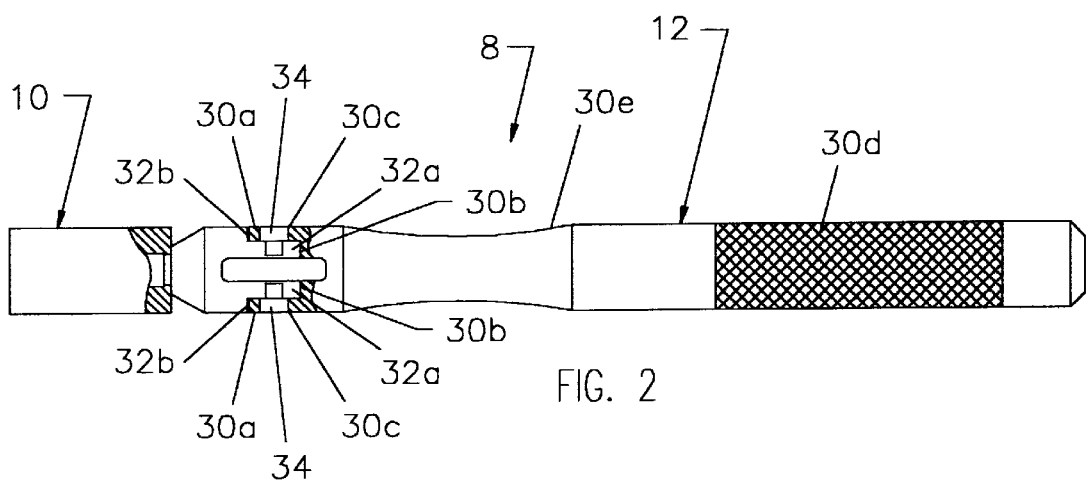
FIG. 2 is a front elevational view of the FIG. 1 tool, with a portion shown in cross section.
Figure 3:
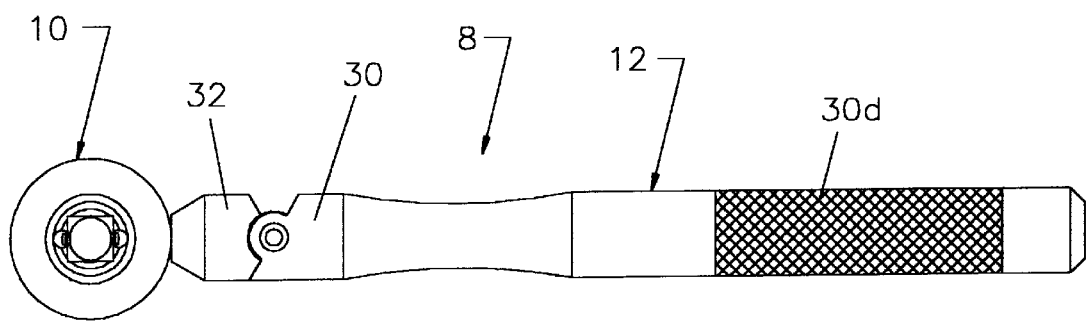
FIG. 3 is a bottom plan view of the FIG. 1 tool.
Figure 4A:
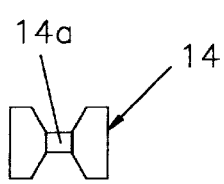
FIG. 4a is top plan view of a precalibrated insert usable with the FIGS. 1–3 tool.
Figure 4B:
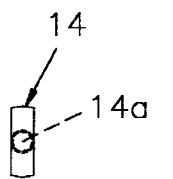
FIG. 4b is a side elevational of the FIG. 4a insert.
Figure 4C:
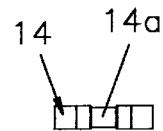
FIG. 4c is a front elevational view of the FIG. 4a insert and FIG. 4d is a top plan view of a nonfrangible insert useful in the FIGS. 1–3 tool.
Figure 4D:
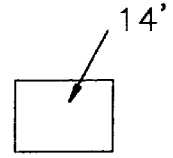
Figure 5:
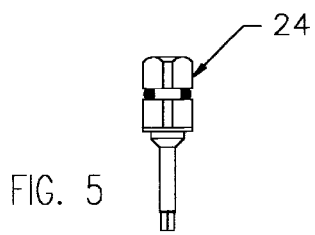
FIG. 5 is front elevational view of a driving tool useful with the FIGS. 1–3 tool.
Figure 6:
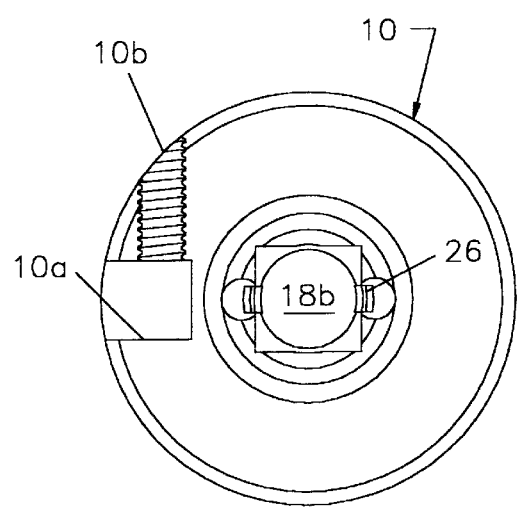
FIG. 6 is a top plan view of a standard ball bearing driver ratchet head used in the FIGS. 1–3 tool and shown in greater detail than in FIGS. 1–3.
Figure 7:
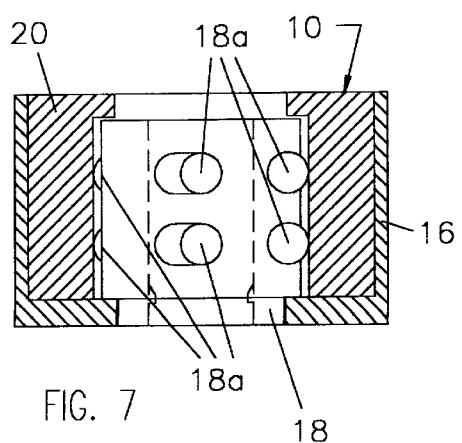
FIG. 7 is a front elevational view, partly in cross section of the FIG. 6 ratchet head.
Figure 8:
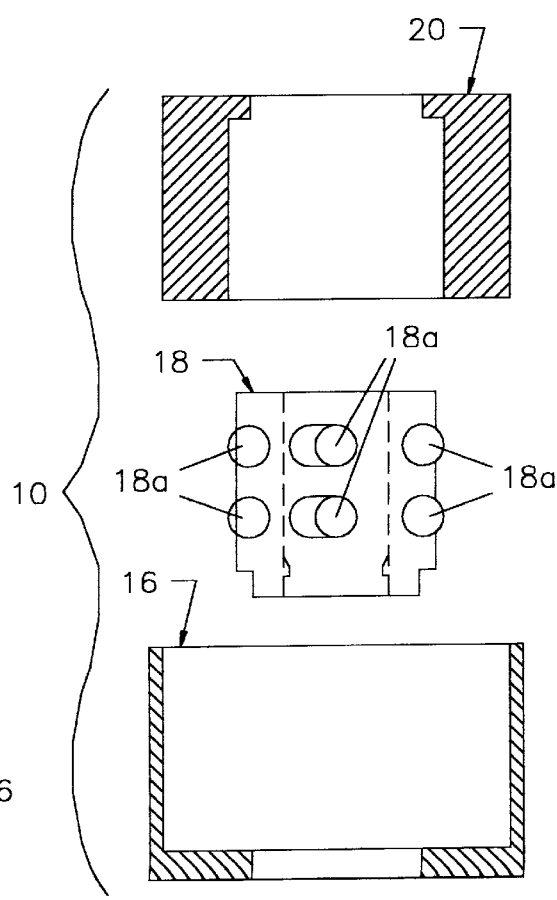
FIG. 8 is a blown apart elevational view of the FIG. 7 ratchet head.

With reference to FIGS. 1–3 a torque ratchet, in the form of a driver head and handle 8 is made up of a standard ball bearing driver ratchet head 10, a pivot arm driver handle 12, and a plastic disposable break-a-way insert 14 (FIGS. 4a–4c). Ratchet head 10, shown in greater detail in FIGS. 6–8, comprises an outer casing 16, an internal ratchet square driver ring 18, ball bearings 18a and an assembly inner casing 20. Incorporated into the inner drive ring 18 of the ratchet head is an internal driver square 18b that is formed in the inner drive ring and accepts the standard square driving tool 24 for screwing down, or unthreading, an abutment or prosthetic screw. Also incorporated in the inner drive ring 18 is a tool holding and driving spring 26 used to snap over and secure the standard square driver tool 24. An internally formed square 10*a* and a tapped cross hole 10*b* are located in the center of the assembled ratchet head 10 as a means for attaching head to pivot arm driver handle 12.

The pivot arm driver handle 12 is made up of two independent components, the main driver arm 30 and the ratchet head attachment arm handle 32. A pair of spaced ears 30*a* and contiguous ear seats 30*b* (see FIG. 2) are formed at a distal end of driver arm 30 which interdigitate with a complimentary pair of spaced ears 32*a* and contiguous ear seats 32*b* formed at a distal end of arm handle 32. These two independent ratchet arm handle components are securely assembled using two press fit fixation pins 34 pivotably received through respective bores 30*c* in ears 30*a* and press fit in respective bores 32*c* in ears 32*a*. The main driver handle 30 is machined with a medium knurl 30*d* and a defined radius groove 30*e* for easy functional use. A half center groove or recess 30*f*, 32*f*, respectively, is formed intermediate to the ears and ear seats of each respective pair of driver arm 30 and arm handle 32 to form an insert receiving chamber 12*a* (FIG. 2). The assembly of these two handle components, 30 and 32, with the press fit fixation pins 34 allow the assembled ratchet arm handle 30 to pivot freely, relative to attachment arm handle 32, in a singular 60 degree angular clockwise direction limited by the interaction of stop surfaces 30*g*, 32*g* as seen in FIG. 1. At the opposite end of the ratchet head attachment arm handle 32 is a machined square 32*h* that locates and snaps into the mating broached square 10*a* of the assembled ratchet head 10. This defined snap connection 32*h* and 10*a* together with the tapped cross hole 10*b* on the assembled ratchet head 10 allow a user to remove the pivot arm driver handle 12 and use the ratchet head as a finger driver.

The assembled torque ratchet wrench handle has been designed to deliver a precalibrated application torque by inserting a plastic, disposable break-a-way insert 14 into the assembled chamber 12*a* of the pivot arm handle. Insert 14 is machined with a selected, defined center groove 14*a* that is specific to the required application torque. Once the defined torque is reached by the ratchet tool, the insert 14 will fracture at its reduced depth center 14*a* and the main driver handle 30 will break-a-way and rotate freely up to 60 degrees in the clockwise direction as seen in FIG. 1.

A selected color pigment can be given to each plastic insert as a means of identifying the defined torque application. To guarantee that the plastic insert 14 delivers the precise application torque, the assembled grooved area 12*a* is machined with a defined stop 30*i*, 32*i* respectively, to center the insert 14 in the assembled pivot arm area. If a predefined application torque is not necessary, a solid metal insert 14', shown in FIG. 1*d*, can be used and the tool will fimction as a straight ratchet wrench.

The invention may take on other various forms without departing from the spirit or essential character thereof and the disclosed embodiment is meant to be illustrative and not limiting, the scope of the invention being indicated by the appended claims.

What is claimed:

1. A torque tool for applying a defined, selected amount of torque to a threaded member comprising:

first and second handle members each having a first and second end portion, the first end portion of each end handle member being pivotably mounted together, the second end portion of one of the two handle members having a torque applying head for applying torque to a threaded member, a chamber formed between first end portions of the first and second handle members and an insert member received in the chamber for transferring force from one handle member to the other handle member, the insert being frangible at a defined level of torque.

2. A torque tool according to claim 1 in which the insert is formed of a plastic material and configured to have a narrowed neck portion selected to break at a selected level of torque.

3. A torque tool according to claim 2 in which the chamber is formed with a stop surface in each handle member to ensure consistent placement of inserts within the chamber.

4. A torque tool according to claim 1 in which one handle member is allowed to rotate freely relative to the other handle member for up to a selected portion of a rotation cycle when there is no unbroken insert in the chamber.

5. A torque tool according to claim 4 in which the selected portion of a rotation cycle is 60 degrees.

6. A torque tool according to claim 1 further including a metal insert for converting the torque tool to one in which the insert will not fracture.

7. A torque tool according to claim 1 in which the tool is a wrench.

8. A torque tool according to claim 1 in which the torque applying head comprises an internal ratchet square driver ring and a holding spring mounted within the driver ring for holding and driving a square driver tool.

9. A torque tool for applying a defined, selected amount of torque to a threaded member comprising:

first and second handle members each having a first and second end portion, the second end portion of one of the two handle members having a torque applying head for applying torque to a threaded member, a pair of spaced ears and a pair of spaces ear seats formed at the first end portion of each of the two handle members, a recess formed intermediate to each pair of ears and ear seats, the first and second handle members pivotably mounted together by interdigitating the pairs of ears with the ears received in respective ear seats and with the recesses aligned and in communication with each other to form a chamber, the chamber having an insert receiving opening at a side thereof, the first handle member being pivotable relative to the second handle member for a selected portion of a rotational cycle with the configuration of the chamber changing upon such pivotal movement, and an insert member for reception in the chamber for transferring force from one handle member to the other handle member, the insert member preventing pivotal motion between the first and second handle members with concomitant changing in the configuration of the chamber when the insert member is received in the chamber, the insert being frangible at a defined level of torque.

10. A torque tool according to claim 9 in which the insert is formed of a plastic material and configured to have a narrowed neck portion selected to break at a selected level of torque.

11. A torque tool according to claim 9 in which the chamber is formed with a stop surface in each handle member to ensure consistent placement of inserts within the chamber.

* * * * *